United States Patent [19]

Trawinski et al.

[11] Patent Number: 4,921,792
[45] Date of Patent: May 1, 1990

[54] CONTINUOUS CELL DISPERSION, CULTIVATION AND SUBSTANCE RECOVERY PROCESS

[75] Inventors: Jurgen Trawinski, El Sobrante; Detmar Redeker, Emeryville, both of Calif.

[73] Assignee: Miles Inc., Elkhart, Ind.

[21] Appl. No.: 126,049

[22] Filed: Nov. 27, 1987

[51] Int. Cl.$^5$ .................. C12P 3/00; C12P 21/00; C12N 5/02
[52] U.S. Cl. .................. 435/41; 435/240.25; 435/240.27; 435/803; 435/813; 435/70.21; 435/70.3
[58] Field of Search .......... 435/41, 68, 240.25, 435/240.26, 240.27, 286, 311, 803, 813; 210/181, 258, 321.79, 321.8, 500.22, 500.23

[56] References Cited

U.S. PATENT DOCUMENTS 4,722,902 2/1988 Harm et al. .................. 435/311
4,780,205 10/1988 Murakami et al. .................. 210/321.8
4,806,484 2/1989 Petrossian et al. .................. 435/311

FOREIGN PATENT DOCUMENTS 0201086 11/1986 European Pat. Off. .................. 435/286

Primary Examiner—Barry S. Richman
Assistant Examiner—William H. Beisner
Attorney, Agent, or Firm—James A. Giblin

[57] ABSTRACT

A system for continuous production and removal of a biological substance from a dispersed cell culture. The system comprises a reactor adapted to maintain the cell culture under incubating conditions and means for pumping limited volumes of the culture fluid from the reactor and through an external substance separation device adapted to extract the substance in a limited time on a continuous basis without collection of, or damage to, the dispersed cells. Less than 5% of the total culture fluid volume is outside the reactor (Volume outside or Vo) at any time and a given dispersed cell is outside the protective environment of the reactor for less than about two minutes, as expressed by the following relationship, $$\frac{Vo(ml)}{\text{pump rate}(ml/min)} \leq 2 \text{ minutes.}$$

In preferred embodiments the external device comprises a plurality of substance-extracting, porous, hollow fibers through which the culture fluid, substance, and dispersed cells are continuously passed. In other preferred embodiments, separate means for continuously dialyzing the culture fluid prior to its return to the reactor are provided.

14 Claims, 5 Drawing Sheets

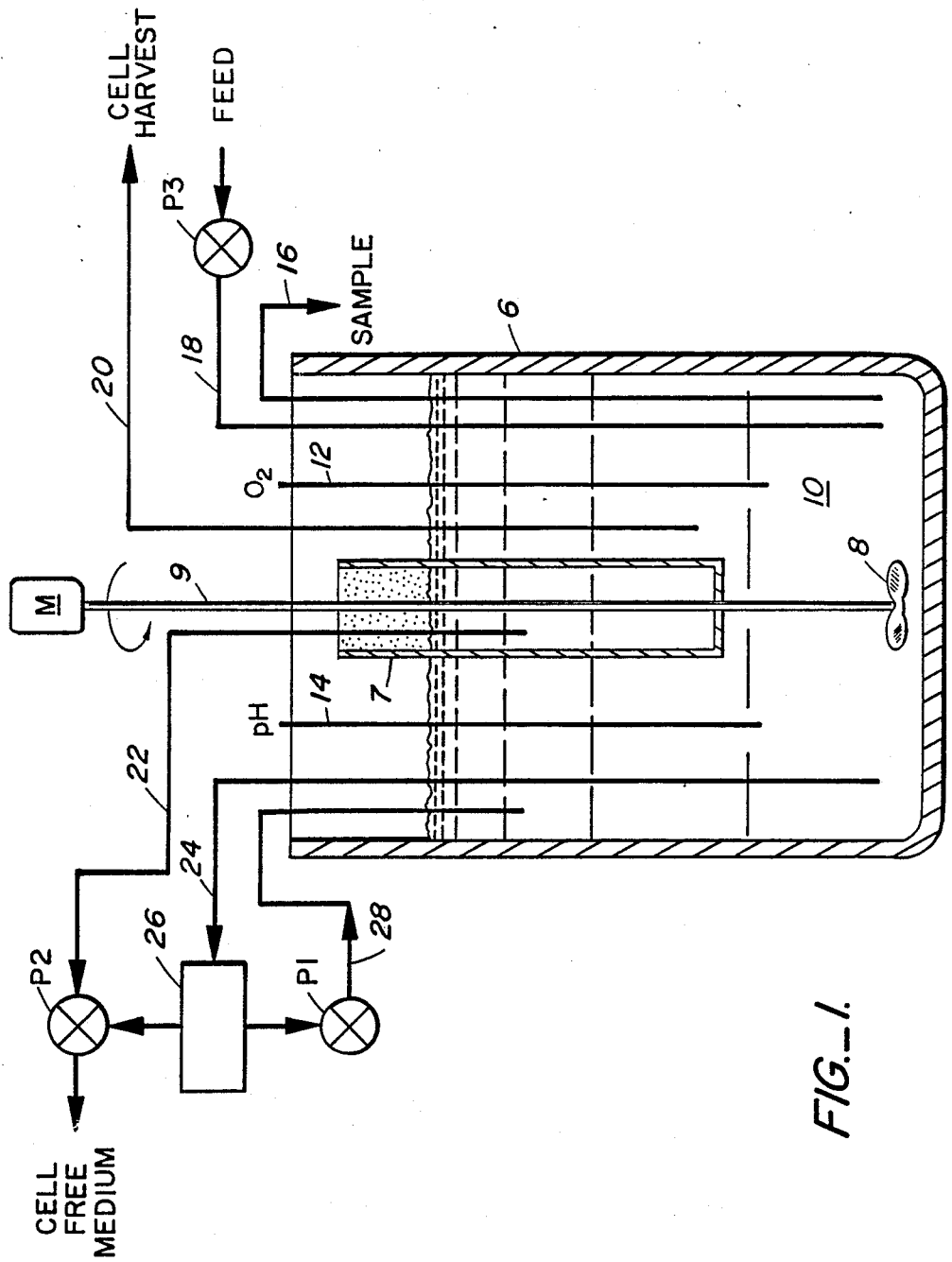
FIG._1.

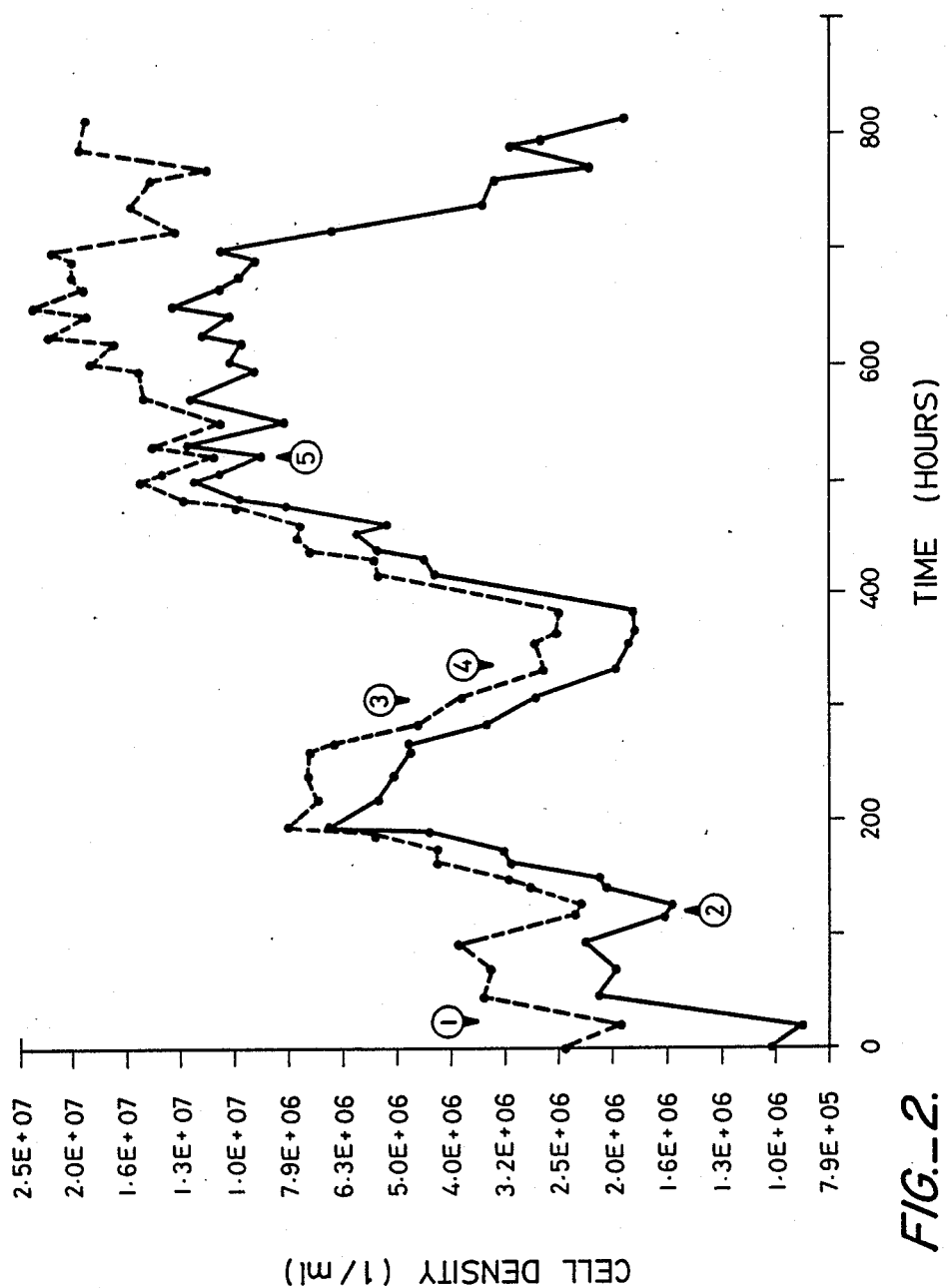
FIG._2.

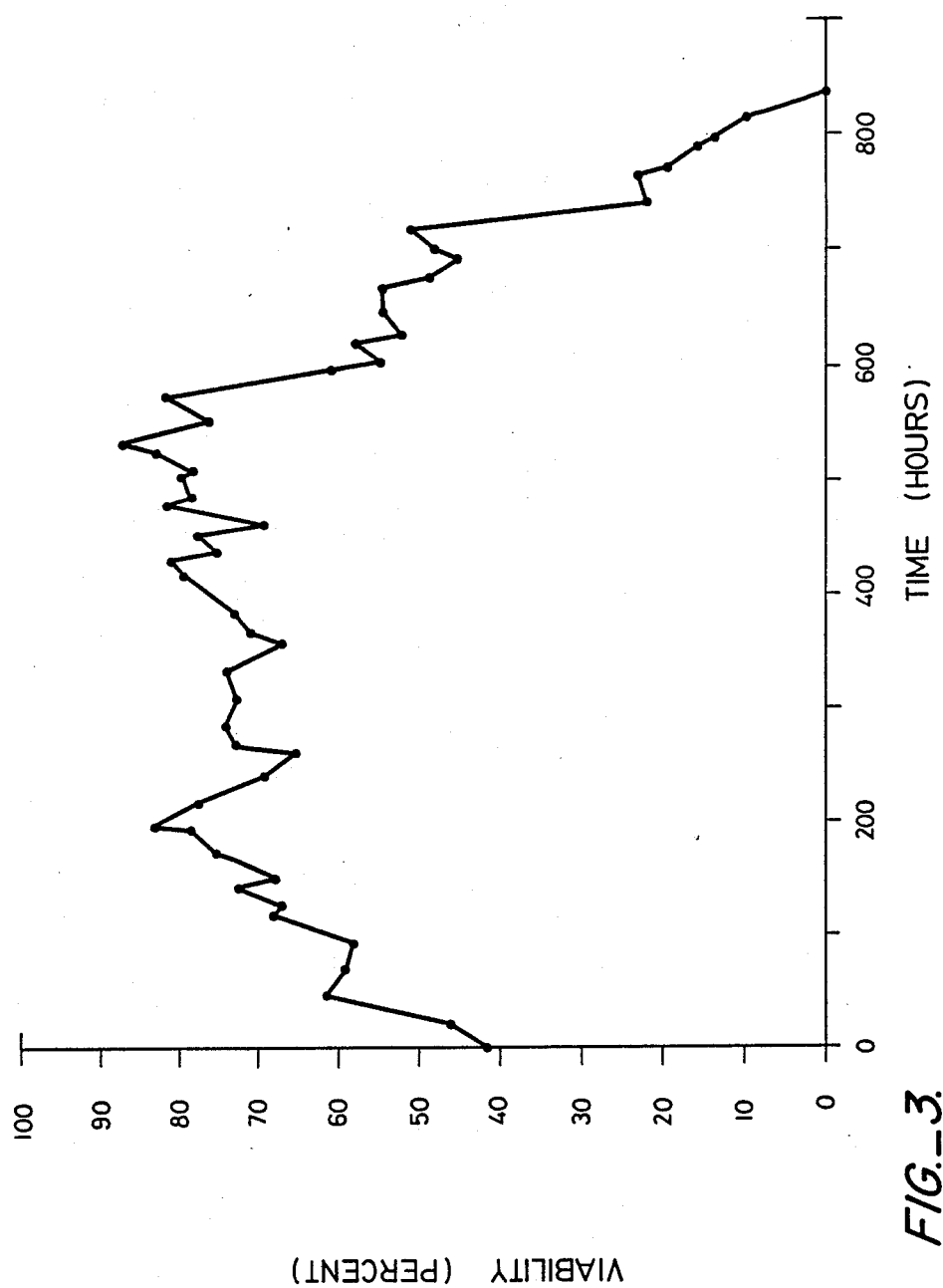
FIG._3.

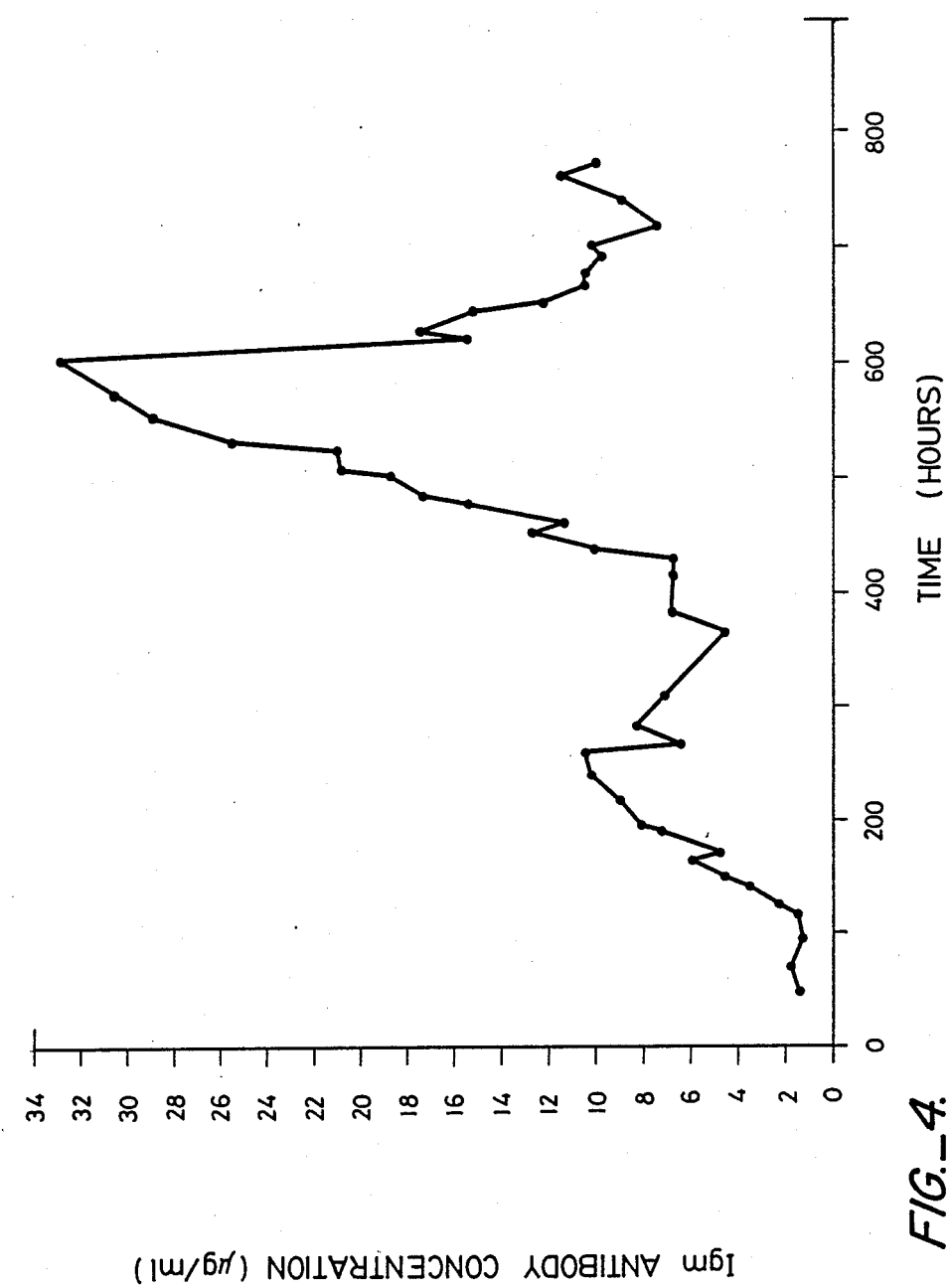
FIG._4.

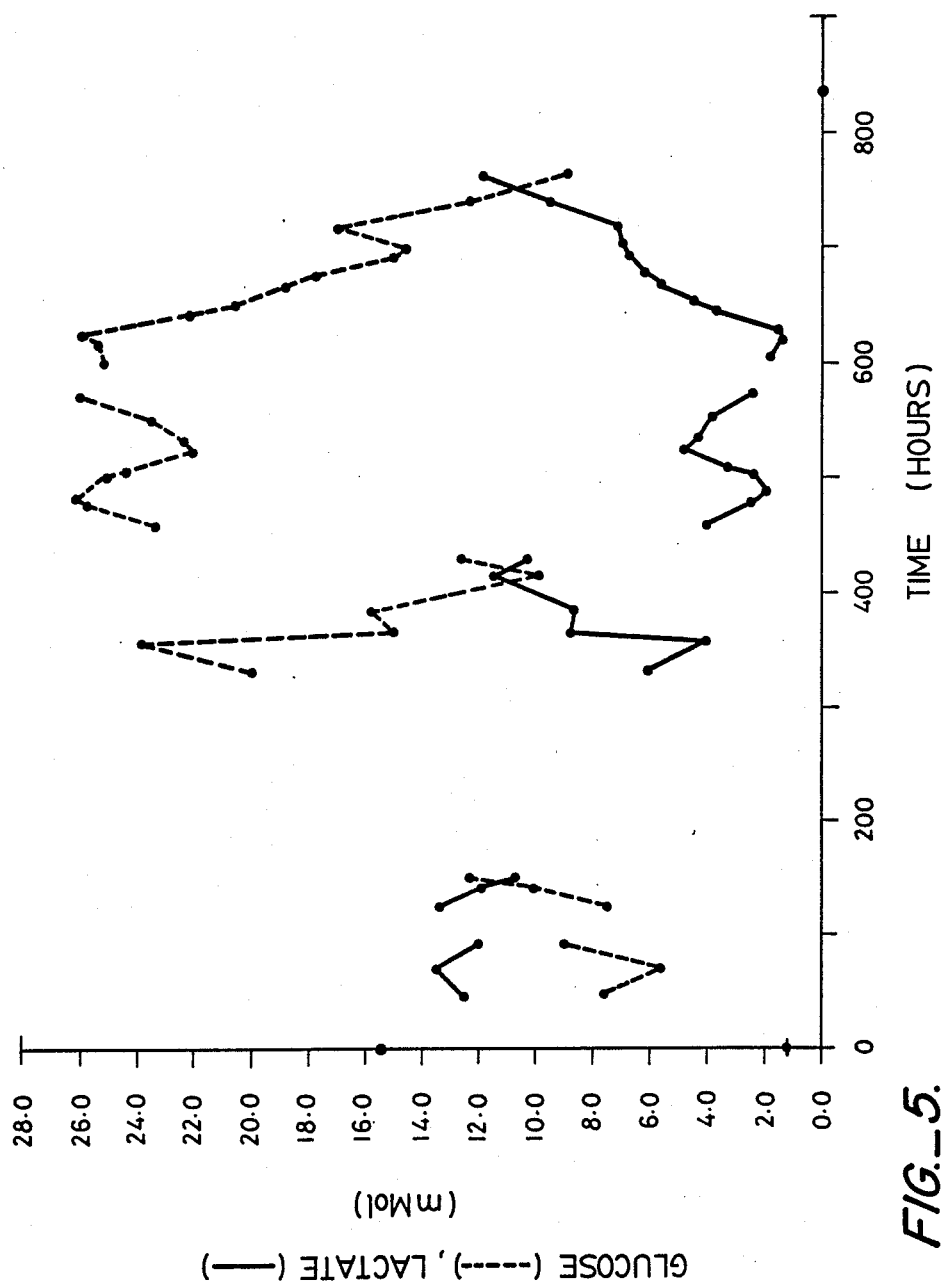
FIG._5.

CONTINUOUS CELL DISPERSION, CULTIVATION AND SUBSTANCE RECOVERY PROCESS

BACKGROUND OF THE INVENTION

1. Field

This disclosure is concerned generally with cell culture systems and specifically with a system adapted to produce and extract biological substances on a continuous basis from continuously dispersed cells without significant damage to the cells.

2. Prior Art

The cultivation of selected cells to produce useful substances has been practiced for many centuries. Improvements have been developed over the years and many of these improvements focus on systems or devices adapted for the continuous production of given biological substances from a cell culture. Examples of such continuous systems are described, for example, in U.S. Pat. No. 4,166,768 to Tolbert et al (combined reactor and substance filter unit) and U.S. Pat. No. 4,178,209 to Tolbert et al (also showing a combined cell culture reactor and substance filtering unit). See also recent U.S. Pat. No. 4,639,422 to Geimer et al (cell culture filter apparatus for the continuous cultivation and harvesting of biological products from a dispersion of mammalian cells), Large Scale Cell Culture in Biotechnology by W. R. Arathoon and J. R. Birch, Science, Vol. 232, pp. 1390–1395, 1986 (discussing problems associated with scaling up of mammalian cell production), and A Radial Flow Hollow Fiber Bioreactor for the Large-Scale Culture of Mammalian Cells, by J. P. Tharaken and P. C. Chau, Biotech. & Bioeng., Vol. XVIII, pp. 329–342, 1986.

With the relatively recent discoveries based on recombinant DNA and monoclonal antibody technologies, increasing attention has been directed to providing cell culturing systems that can produce useful biological substances on a continuous basis. In an ideal system, the great majority of the cells are not damaged, are maintained in an optimum environment for expression of the biological substances, the substance yield is acceptable, and the system has a reasonably long and economically useful life. Although many of the cell culture systems disclosed to date achieve one or more of the above goals, it is difficult to achieve all of the above goals simultaneously in a single system. This is especially true for mammalian cell culture systems, because of their known sensitivity, especially to changing environments. Given the increased attention now being directed to mammalian cell lines for the production of both monoclonal antibodies and biological substances based on recombinant DNA techniques, the achievement of all of the above goals in a single mammalian cell culture system is highly desirable.

Although the scale up of mammalian cells still is considered difficult, several additional cell culture systems have been proposed. To simultaneously reach high cell densities and harvest the product released into the cell culture medium, systems are available that in one way or the other suspend or immobilize the cells to be cultured. Hollow-fiber cartridges for suspended cells (see European Patent Application No. 0 112 155, assigned to BioResponse, Inc.) as well as ceramic cartridges for immobilized cells (see B. G. D. Bodeker et al, Develop. Biol. Standard, Vol. 66, pp. 473–479 [S. Karger, Basel, 1987]) are now used for suspended cells or to immobilize cells which are then perfused with the cell culture medium. An advantage of these systems is that product can be harvested from a medium that contains only a low number of cells or no cells at all.

Several attempts have been made to adapt the deep tank fermentor technology used for microbial fermentation to the cultivation of mammalian cells. Both anchorage dependent and independent cells have been grown in deep tank fermentors. Amongst others, however, one key problem is to establish a continuous culture. Traps and spinning filters have been used to separate the product containing medium from the cells and to allow a long term cultivation process. Unfortunately, however, both processes have been shown to be less efficacious than expected. The spinfilters tend to clog and afterwards do not allow medium to penetrate. Such high density reactors are therefore difficult, if not impossible, to use with existing technology.

The approach described in this disclosure avoids many of the above problems. In one embodiment, the system of this disclosure limits the amount of dispersed cell culture and its duration outside of the reactor. A preferred system also facilitates the continuous dispersion of the cells by continuously breaking up cell aggregates and uses an external filtering device such as a hollow fiber membrane with having a controlled average pore size (e.g. 0.6 um pore size) to separate the substance to be harvested with the medium from the circulating cells. The outside-the-reactor placement of the filter or porous hollow fiber device permits control over the volume of culture outside the reactor at any one time and the length any one dispersed cell is outside the reactor. The device is located outside of the fermentor and can be easily replaced when the membrane is clogged and penetration of substance and medium is no longer obtained. Details of our system are described below.

SUMMARY OF THE INVENTION

The cell culture system of this disclosure comprises a reactor adapted to maintain a dispersion of cells in a culture fluid under conditions sufficient to assure the continuous expression of a useful biological substance such as monoclonal antibodies or other proteins from the cells. In continuous communication with, but separate from the reactor, is a substance separating device capable of extracting the expressed substance (e.g. antibodies), but not the dispersed cells, from the culture fluid passing through it and back into the reactor. A relatively small volume of culture fluid (and dispersed cells) is outside the controlled environment of the reactor at any given time. A given dispersed cell is outside the reactor for less than two minutes.

In further preferred embodiments the culture fluid is replenished with nutrients and waste products are removed by an in-line dialysis unit prior to its return to the reactor. In addition, the system is adapted to disperse cellular aggregates, when necessary, without damage to the cells as the minimal volume of culture fluid is moved out of the reactor through the separating and dialysis devices, and back to the reactor.

In general, the volume of culture fluid outside of the reactor at any one time is less than about 5% (generally in the range of 2–5%) of the total culture fluid in the system. The actual volume of fluid outside the reactor, of course, depends on the total fermentor volume. In our illustrative system, this volume (outside the reactor) is in the range of about 200–300 ml. This means that at one time, a given suspended cell is outside the reactor for less than about 2 minutes (using a pump rate of about 100-150 ml/min. for an outside culture fluid volume (Vo) of 200-300 ml). This important relationship can be expressed as $$\frac{Vo(ml)}{pump\ rate(ml/min.)} \leq 2\ minutes.$$

By using the above low volume and short time outside the reactor, the system of this disclosure permits minimal loss of control over such important variables as $O_2$, pH, nutrient loss, waste gain, eetc. In our system, the nutrient source is as far away from the site of nutrient loss (substance collection device) as possible. This minimizes nutrient loss through the substance collecting device.

A preferred separating or filtering device comprises porous hollow fibers, the average pore size of which allows passage and redirection of the expressed substance and culture fluid but not the expressing cells which continue to circulate back into the system. Since the porous fibers exclude mammalian cells from the continuous collection process, the average pore diameter of the hollow fibers should be in the range of 0.2 to 0.6 um. In preferred embodiments, at least 40%, preferably about 100%, of the substance passing through such fibers is removed from the dispersed cell culture fluid entering the hollow fiber device.

BRIEF DESCRIPTION OF THE FIGURES

FIG. 1 is a schematic view of a preferred system of this disclosure.

FIG. 2 is a graph relating variation of cell density with time in a reactor system of this disclosure.

FIG. 3 is a graph relating cell viability with time in the reactor of this disclosure.

FIG. 4 is a graph relating antibody production with time in the reactor of this disclosure.

FIG. 5 is a graph relating the glucose and lactate production over time in the reactor of this disclosure.

SPECIFIC EMBODIMENTS

An important aspect of this disclosure is that it is concerned with a fermentation reactor suitable for mammalian cell culture and an outside-the-fermentor system for the separation and harvesting of expressed biological product (or biological substance). Another important aspect of this disclosure is that the amount of culture fluid outside of the fermentation reactor is kept small (less than about 5% of the total culture fluid volume). In addition, the dispersed cells are returned to the reactor environment in less than about two minutes, as determined by the above relationship of pump rate and outside volume (Vo) of culture fluid. When certain mammalian cells are used in the system, the cells are not damaged and, in some cases, their function appears to be enhanced by the controlled break up of cell aggregates as they move through the system.

Although it is thought that our system will be useful for a variety of mammalian cell lines in different reactors, in the examples below, we used a stirred deep tank reactor in a perfusion mode. In one set of examples EBV transformed human lymphocytes secreting IgM monoclonal antibodies were cultivated in the stirred deep tank fermentor under serum free conditions.

The whole fermentor was pumped with a peristaltic pump through an external loop and back into the fermentor. In this loop a commercially available porous hollow fiber cartridge was installed. The hollow fiber membrane had an average pore size of 0.6 um and therefore, allowed only medium and substance collected (i.e. IgM antibodies) to penetrate for subsequent removal from the system. The cells were at all times kept in the loop and therefore in the overall fermentor. At no time were the cells away from the reactor for more than two minutes. The pumping was found to be not harmful for the cells and fermentors were continuously run for more than 30 days while being perfused via the external membrane.

Materials and Methods (Monoclonal Antibodies)

Cells and Culture Medium

The human EBV transformed cell line 13Cl (A.T.C.C. No. CRL 8796) which produces IgM monoclonal antibodies (reactive with *Pseudomonas aeruginosa*, Fisher Type 5) was adapted and cultivated in a serum free medium based on a 1:1 mixture of DME and Ham's F12 (Sigma) with the addition of 2 g/L human serum albumin (Miles Inc.) and 10 mg/l human transferrin (Miles Inc.) and 200 u/L bovine insulin (Elanco Products, Co., Division of Eli Lilly Co.). The same medium was used throughout the whole fermentation process.

Cell counts on the fermentor content were obtained twice a day using a hemacytometer and the viability of the cells was assessed using the trypan blue dye exclusion test. Glucose and lactate concentrations were analyzed in the same samples taken for cell counts, using commercially available analyzers.

IgM Testing

A competitive ELISA according to the method described by Kearny et al, J. Immunol. 123, 1548 (1979) was used to determine the amount of IgM in the samples.

The Reactor (fermentor)

The overall fermentor set up included a 5 liter fermentor and can be seen in FIG. 1. FIG. 1 shows a typical set up of the fermentor used in a representative example. The vessel and its headplate were obtained commercially (Virtis). Separation of the fermentor content was carried out with a $O_2/CO_2$/air mixture via 30 feet of silicone rubber tubing located inside the fermentor. Integrity of the system is kept by a head space air pressure of 2 psi. All external lines consist of silastic tubing.

Cell Separation

The fermentor was equipped with a stainless steel spin filter operated at 150 rpm in order to allow perfusion in the start up phase of the experiment.

After 284, hours due to a cloggd spin filter, the cell separation was carried out externally with a Plasmapur ® hollow fiber cartridge (obtained from Organon Teknika, BV).

The fermentor content was then pumped through a silastic tubing with the aid of a masterflex peristaltic pump. A Plasmapur ® hollow fiber cartridge was put into this loop and the cell suspension was pumped through the inner lumen of the fibers at 150 ml/min. The membrane of the fibers consists of Plasmaphan PIH with a 0.65 um pore size and a 0.07 $m^2$ effective surface area. A pressure gauge in front of the Plasmapur cartridge was used to determine increasing pressure in the cartridge, indicating when the membrane started to clog.

The culture medium to be harvested was continuously withdrawn from the extra capillary space of the Plasmapur cartridge using a second masterflex pump ($P_2$) with a 7015.20 pumphead. The maximal volume of medium harvested via the Plasmapur was 4.5 L per day to 106% of the fermentor volume.

A third Masterflex pump ($P_3$), set to the same delivery rate as the harvest pump, was used to feed fresh serum free medium into the fermentor.

Our overall system is illustrated by FIG. 1. There, dispersed cell culture 10 is maintained in stirred tank reactor 6 with continuous stirring provided by stirrer 8 driven by motor M via shaft 9. In early work, a spin filter 7 was used as a cell separator so that cell-free culture containing dissolved substance could be pumped directly via tubing 22 by pump $P_2$ for further purification. Unfortunately, the spin filter 7 tended to clog after 200-300 hours, thus leading to its removal and the present invention in which cell-containing culture fluid and substance 10 is pumped directly from reactor 6 via tubing 24 by pump $P_1$ through external hollow fibers device 26 and back to the reactor 6 via tubing 28. Devices for monitoring pH, $O_2$ and for replenishing culture medium (feed via pump $P_3$) are provided as shown in FIG. 1. Culture fluid samples may be periodically taken via tubing 16.

Results (Continuous Monoclonal Antibody Production)

Effect of pumping on cell growth and viability. The fermentor (#86041) was inoculated with 3 L culture at $10 \times 10^5$ cells/ml with 46% viability. The fermentor was initially equipped with a stainless steel spin filter through which cell free fermentor content was removed at a rate of 90 ml/hr i.e. 2.2 L or 73% medium exchanged per day. This perfusion rate was held constant and resulted in increased viability (FIG. 3) and a cell density of about $2 \times 10^6$/ml (FIG. 2). 120 hours after inoculation pumping of the culture with the masterflex pump was started through the external Plasmapur ® at a rate of 100-150 ml/min. The perfusion rate was held at 73% medium exchange per day through the spinfilter during this time. FIGS. 2 and 3 show that the viability and the cell density, both increase almost immediately after the start of the pumping. Both increase and reach a higher plateau than before, resulting in an average of 75% for the viability and about $5 \times 10^6$/ml for the cell density. FIG. 2 shows the total and viable cell density of 13Cl cells in fermentor #86041 during the 800 hours of the experiment.

Samples were taken out of the fermentor at the times indicated, and the cell density was determined using a hemacytometer. The viability was determined using the trypan blue exclusion test.

1 = perfusion via spinfilter at 73% medium exchange per day
2 = start of continuously pumping the whole culture with a masterflex pump at 100 ml/min
3 = spinfilter clogged
4 = perfusion via Plasmapur ® hollow fiber cartridge
5 = change of the perfusion medium to serum free medium without HSA The above five changes apply to FIGS. 3-5.

Cell aggregates that were present in the fermentor before the pumping was started were not present afterwards. Cell density and viability were constant until the spinfilter clogged after 284 hours in the run and cells were lost due to the resulting chemostat. FIG. 3 shows viability of 13Cl cells in fermentor #86041 during the entire 800 hours of the experiment.

Samples were taken out of the fermentor at the times indicated in FIG. 3, and the viability was determined using the trypan blue exclusion test.

Perfusion via Plasmapur ® Separator 70 hours after the first signs of a clogging of the spinfilter the perfusion was restarted via the Plasmapur separator. Due to the clogged spinfilter the fermentor volume had increased to 4.5 L and the cell density was decreased to $2 \times 10^6$/ml at 68% viability. The perfusion rate was set to 200 ml/hour i.e. 4.8 L or 106% medium exchange per day. The cell density responded immediately to the new perfusion conditions. As shown in FIG. 2 the cell density reached a new plateau of $10-13 \times 10^6$ viable cells/ml at 100 hours after the start of the perfusion with the Plasmapur. The Plasmapur separator showed no sign of clogging for over 300 hours indicated by a constant pressure of 50-70 mm Hg in front of the cartridge. 700 hours after inoculation the Plasmapur separator clogged and did not allow further perfusion. Due to the high cell density the culture responded immediately with decreasing viability (FIG. 3) and was discontinued 4 days later.

Product Release

The cell line used secretes IgM monoclonal antibodies into the culture medium. The IgM concentration in the harvested medium is shown in FIG. 4. As with the viable cell count, the IgM concentration increases after perfusion started with the Plasmapur separator, thus indicating that the release of IgM into the medium is cell density dependent. A preferred cell density is $5-10 \times 10^6$/ml under perfusion conditions. In order to evaluate the effects of medium components on the IgM release, 500 hours after inoculation the HSA concentration in the feed medium was decreased from 2 g/L to 0 g/L. Due to the high cell density this did not have any effect on the viability of the cells but the IgM concentration was reduced to 50% of the concentration reached before changing the medium protein content. FIG. 4 shows the amount of IgM secreted into the medium by 13Cl cells in fermentor #86041 during the 800 hours of the experiment. As indicated above, samples were taken out of the fermentor at the times indicated, and the IgM concentration was determined with a competitive ELISA.

Metabolic Activity of the Cells

To measure the metabolic activity of the cells under the various culture conditions, the glucose consumption and lactate production were measured. FIG. 5 shows that under perfusion with the spinfilter the glucose and the lactate concentration in the fermentor are both at about 11 mMol due to the relatively low cell density. After the perfusion with the Plasmapur ® was started the cell density increased and both the glucose consumption and the lactate production were enhanced. During the cell density plateau at $10-13 \times 10^6$ vc/ml, an average glucose concentration of 25 mMol and an average lactate concentration of 3 mMol were reached. FIG. 5 shows the concentration of lactate and glucose in fermentor #86041 during the 800 hours of the experiment.

Discussion

The work presented in the above examples shows the modification of a deep tank fermentor for the cultivation of human EBV transformed lymphocytes. Other fermentation reactors can be used (e.g. air lift fermentors, hollow fiber bioreactors and the like). The perfusion set up includes an externally located porous hollow fiber system that allows the maintenance of a high cell density (up $10-13 \times 10^6$ viable cells/ml) perfusion reactor. It was shown that the pumping of the cells with a masterflex peristaltic pump, which is preferred for this set up, does not harm the cells, but at least in this example, even increases the viability. Aggregates of cells that were visible in the fermentor before pumping of the culture were not present after pumping. This is probably due to the physical stress on the cell clumps during pumping.

The disruption of the aggregates in the above system seems to allow the single cells to have better access to the medium resulting in better growth and metabolic activity. The stainless steel spinfilter used in the start up phase of the run showed clogging after only 284 hours allowing only a low cell density of $2 \times 10^6$/ml to be reached. Clogging of the spinfilter occurs because of cells and cell debris that settle down in the pores. Because the filter is located inside the fermentor this normally would mean the termination of the cultivation. Use of the Plasmapur ® cartridge allowed a surprisingly higher perfusion rate than the spinfilter for more than 10 days, resulting in a much higher cell density of $13 \times 10^6$/ml. For the same reasons that the spinfilters are clogging, however the Plasmapur membrane also can not be used indefinitely, but the clogging can be minimized by increasing the flow rate of the cell suspension in the fibers.

An added advantage to having the cartridge located outside the fermentor is that it can be replaced by a fresh cartridge without interrupting the experiment (or production). Set ups with several of the Plasmapur cartridges in parallel are possible and this would allow one to switch to a new cartridge after clogging of the first has occurred, thus avoiding interruption.

Further experiments have shown that the set up described here is also suitable for 10-20 L cultures therefore not limited to small fermentors.

Given the above disclosures, it is thought that variations will occur to those skilled in the art. Accordingly, it is intended that the above examples should be construed as illustrative and that the invention disclosed herein should be limited only by the following claims.

We claim:

1. A method of continuously producing and separating a biological substance comprising the steps of:
   (a) introducing into a reactor a dispersed cell culture and incubation fluid which includes a cell population capable of expressing the substance and maintaining the reactor under conditions to assure the expression of the substance;
   (b) continuously moving a portion of the fluid, including dispersed cells and the substance, through a separation device located outside said reactor and continuously separating therein at least some of the substance from the fluid while allowing the majority of the moving fluid and substantially all of the dispersed cells to pass through the separation device, the volume of culture fluid outside of the reactor being less than about 5% of the total culture fluid volume and a given dispersed cell being outside the reactor for less than about two minutes, as determined by the following relationship $$\frac{\text{Volume outside (ml)}}{\text{flow rate (ml/min.)}} \leq 2 \text{ minutes.}$$

2. The method of claim 1 wherein the reactor is a stirred tank reactor and the separating device comprises porous hollow fibers adapted to separate continuously at least about 40% of the substance passing through the device.

3. The method of claim 1 wherein the hollow fibers have an average pore diameter ranging from about 0.2 to 0.6 um.

4. The method of claim 1 wherein the substance is proteinaceous.

5. The method of claim 3 wherein the substance is an antibody.

6. The method of claim 1 wherein means for dispersing cell aggregates are disposed along a flow line positioned between the reactor and the separation device.

7. The method of claim 6 wherein the dispersing means is a pump.

8. A method of continuously producing and separating a biological substance in a cell culture fluid comprising the steps of:
   (a) continuously introducing into a reactor having a recirculatory system a dispersed cell culture fluid which includes a cell population capable of expressing the substance and maintaining the reactor under conditions to assure the expression of the substance;
   (b) continuously moving a portion of the culture fluid including dispersed cells and the expressed substance through a separation device located outside said reactor and continuously separating therein at least some of the substance from the fluid while allowing the moving fluid and the dispersed cells to pass through the separation device;
   (c) continuously returning the fluid and the dispersed cells to the reactor via a recycle loop which includes said separation device; and
   (d) maintaining the total volume of any culture fluid that is outside the reactor in said recycle loop at a given time less than about 5% of the total culture volume and having a given dispersed cell in the volume in said recycle loop for less than about two minutes, as determined by the following relationship $$\frac{\text{Volume of culture fluid in the recycle loop (ml)}}{\text{Flow rate of culture fluid (ml/min)}} \leq 2 \text{ minutes}$$

9. The method of claim 8 wherein the reactor is a stirred tank reactor and the separating device comprises porous hollow fibers adapted to separate continuously at least about 40% of the substance passing through the device.

10. The method of claim 8 wherein the hollow fibers have an average pore diameter ranging from about 0.2 to 0.6 um.

11. The method of claim 8 wherein the substance is proteinaceous.

12. The method of claim 10 wherein the substance is an antibody.

13. The method of claim 8 wherein means for dispersing cell aggregates are disposed within said recycle loop and located between the reactor and the separation device.

14. The method of claim 13 wherein the dispersing means is a pump.

* * * * *